US00PP22816P2

(12) United States Plant Patent

Renvoisé et al.

(10) Patent No.: US PP22,816 P2
(45) Date of Patent: Jun. 26, 2012

(54) *VIBURNUM* PLANT NAMED 'LISAROSE'

(50) Latin Name: *Viburnum tinus*
Varietal Denomination: Lisarose

(76) Inventors: Dominique Renvoisé, Ardon (FR); Gèrard Long, Orleans (FR)

( * ) Notice: Subject to any disclaimer, the term of this patent is extended or adjusted under 35 U.S.C. 154(b) by 32 days.

(21) Appl. No.: 12/925,597

(22) Filed: Oct. 25, 2010

(51) Int. Cl.
*A01H 5/00* (2006.01)

(52) U.S. Cl. ..... Plt./226

(58) Field of Classification Search ..... Plt./226
See application file for complete search history.

(56) References Cited

OTHER PUBLICATIONS

Pluto: Plant Variety Database 2011-04, Citation for *Viburnum* 'Lisarose' retrieved on Dec. 14, 2011. Retrieved from the Internet at <http://upov.int/pluto/en/> 2 pages.*

* cited by examiner

*Primary Examiner* — June Hwu
(74) *Attorney, Agent, or Firm* — C. A. Whealy

(57) ABSTRACT

A new and distinct cultivar of *Viburnum* plant named 'Lisarose', characterized by its broadly upright plant habit; moderately vigorous growth habit; freely branching habit; numerous pink and white-colored flowers; and good garden performance.

3 Drawing Sheets

Botanical designation: *Viburnum tinus*.
Cultivar denomination: 'LISAROSE'.

BACKGROUND OF THE INVENTION

The present invention relates to a new and distinct cultivar of *Viburnum* plant, botanically known as *Viburnum tinus* and hereinafter referred to by the name 'Lisarose'.

The new *Viburnum* plant originated from an open-pollination in 2003 of an unnamed seedling selection of *Viburnum tinus*, not patented, as the female, or seed, parent with an unknown selection of *Viburnum tinus* as the male, or pollen, parent. The new *Viburnum* plant was discovered and selected by the Inventor in 2005 as a single flowering plant within the progeny of the stated open-pollination in a controlled environment in Ardon, France.

Asexual reproduction of the new *Viburnum* plant by softwood cuttings in a controlled environment in Ardon, France since 2005 has shown that the unique features of this new *Viburnum* plant are stable and reproduced true to type in successive generations of asexual reproduction.

SUMMARY OF THE INVENTION

Plants of the new *Viburnum* have not been observed under all possible environmental conditions. The phenotype may vary somewhat with variations in environment such as temperature and light intensity without, however, any variance in genotype.

The following traits have been repeatedly observed and are determined to be the unique characteristics of 'Lisarose'. These characteristics in combination distinguish 'Lisarose' as a new and distinct cultivar of *Viburnum* plant:

1. Broadly upright plant habit.
2. Moderately vigorous growth habit.
3. Freely branching habit.
4. Numerous pink and white-colored flowers.
5. Good garden performance.

Plants of the new *Viburnum* can be compared to plants of the female parent selection. Plants of the new *Viburnum* differ from plants of the female parent selection in the following characteristics:

1. Leaves of plants of the new *Viburnum* are glossier than leaves of plants of the female parent selection.
2. Plants of the new *Viburnum* have darker pink-colored flower buds than plants of the female parent selection.
3. Plants of the new *Viburnum* are more freely flowering than plants of the female parent selection.

Plants of the new *Viburnum* can be compared to plants of *Viburnum tinus* 'Gwenllian', not patented. Plants of the new *Viburnum* differ from plants of 'Gwenllian' in the following characteristics:

1. Leaves of plants of the new *Viburnum* are glossier than leaves of plants of 'Gwenllian'.
2. Plants of the new *Viburnum* have darker pink-colored flower buds than plants of 'Gwenllian'.
3. Plants of the new *Viburnum* are more freely flowering than plants of 'Gwenllian'.

BRIEF DESCRIPTION OF THE PHOTOGRAPHS

The accompanying colored photographs illustrate the overall appearance of the new *Viburnum* plant showing the colors as true as it is reasonably possible to obtain in colored reproductions of this type. Colors in the photographs may differ slightly from the color values cited in the detailed botanical description which accurately describe the colors of the new *Viburnum* plant.

The photograph on the first sheet is a side perspective view of a typical plant of 'Lisarose' grown in a container.

The photograph on the second sheet is a close-up view of a typical inflorescence of 'Lisarose'.

The photograph on the third sheet is a close-up view of a typical leaf of 'Lisarose'.

DETAILED BOTANICAL DESCRIPTION

The aforementioned photographs and following observations, measurements and values describe plants of the new

*Viburnum* grown during the early spring in five-liter containers in an outdoor nursery in Boskoop, The Netherlands and under conditions which closely approximate commercial *Viburnum* production. During the production of the plants, day temperatures ranged from 7° C. to 15° C. and night temperatures ranged from 2° C. to 8° C. Plants were four years old when the photographs and the description were taken. In the description, color references are made to The Royal Horticultural Society Colour Chart, 2007 Edition, except where general terms of ordinary dictionary significance are used.

Botanical classification: *Viburnum tinus* 'Lisarose'.

Parentage:

*Female, or seed, parent*.—Unnamed seedling selection of *Viburnum tinus*, not patented.

*Male, or pollen, parent*.—Unknown selection of *Viburnum tinus*, not patented.

Propagation:

*Type*.—By softwood cuttings.

*Time to initiate roots*.—About one month at 20° C.

*Time to produce a rooted young plant*.—About five months at 18° C.

*Root description*.—Medium in thickness, moderately fibrous; close to 164B in color.

*Rooting habit*.—Moderate branching; medium density.

Plant description:

*Plant form and growth habit*.—Evergreen perennial shrub; broadly upright plant habit; moderately vigorous growth habit.

*Branching habit*.—Freely branching habit with about 17 primary lateral branches; pinching (removal of terminal apices) will enhance lateral branch development.

*Plant height*.—About 58.8 cm.

*Plant diameter* (*area of spread*).—About 51.3 cm.

Lateral branch description:

*Length*.—About 21.5 cm.

*Diameter*.—About 4 mm.

*Internode length*.—About 2.6 cm.

*Texture*.—Smooth, glabrous.

*Strength*.—Strong.

*Color, developing*.—Close to 144A and 146A.

*Color, developed*.—Close to 197A to 197B and 199B.

Foliage description:

*Arrangement*.—Opposite, simple.

*Length*.—About 6.3 cm.

*Width*.—About 4.1 cm.

*Shape*.—Ovate.

*Apex*.—Acute, slightly recurved.

*Base*.—Cordate.

*Margin*.—Entire; slightly to moderately undulate.

*Texture, upper and lower surfaces*.—Sparsely pubescent.

*Venation pattern*.—Pinnate.

*Color*.—Developing leaves, upper surface: Close to 137A to 137B. Developing leaves, lower surface: Close to 137C to 137D. Fully expanded leaves, upper surface: Close to N137A; venation, close to 146D. Fully expanded leaves, lower surface: Close to 147B; venation, close to 145A.

*Petiole*.—Length: About 1.1 cm. Diameter: About 2 mm. Texture, upper and lower surfaces: Smooth, glabrous. Color, upper and lower surfaces: Close to 146D.

Flower description:

*Flower appearance/arrangement*.—Single rotate flowers arranged in terminal and axillary branched umbels; freely flowering habit with usually about 48 flowers per inflorescence; flowers face mostly upright.

*Natural flowering season*.—Continuous flowering from March into May in The Netherlands; flowers begin flowering about nine months after planting.

*Flower longevity*.—About two weeks days on the plant; flowers not persistent.

*Fragrance*.—None detected.

*Inflorescence height*.—About 4.6 cm.

*Inflorescence diameter*.—About 5 cm.

*Flower diameter*.—About 7 mm.

*Flower depth* (*height*).—About 6 mm.

*Flower buds*.—Length: About 3 mm. Diameter: About 3 mm. Shape: Flattened globular. Color: Close to NN155D flushed with close to 63B and 186B.

*Petals*.—Quantity per flower: Single whorl of five. Length: About 4 mm. Width: About 3.5 mm. Shape: Obovate. Apex: Obtuse. Base: Fused. Margin: Entire. Texture, upper and lower surfaces: Smooth, glabrous. Color: When opening and fully opened, upper surface: Close to NN155D. When opening and fully opened, lower surface: Close to NN155B flushed with close to 63B and 186B.

*Sepals*.—Quantity per flower: Single whorl of five. Length: About 1 mm. Width: About 1 mm. Shape: Deltoid. Apex: Acute. Base: Fused. Margin: Entire. Texture, upper and lower surfaces: Smooth, glabrous. Color: When opening and fully opened, upper surface: Close to 187B. When opening and fully opened, lower surface: Close to 187B.

*Peduncles*.—Length: About 1.9 cm. Diameter: About 2.5 mm. Strength: Moderately strong. Texture: Smooth, glabrous. Color: Close to 176B and 177A.

*Pedicels*.—Length: About 3 mm. Diameter: About 0.75 mm. Strength: Moderately strong. Texture: Smooth, glabrous. Color: Close to 177B to 177C.

*Reproductive organs*.—Androecium: Quantity per flower: About five. Filament length: About 2.5 mm. Filament color: Close to 157D. Anther shape: Reniform. Anther length: About 0.5 mm. Anther color: Close to 145C to 145D. Amount of pollen: Scarce. Pollen color: Close to 157D. Gynoecium: Quantity per flower: One. Pistil length: About 1.5 mm. Style length: About 1 mm. Style color: Close to 155D. Stigma shape: Lobed. Stigma color: Close to NN155D. Ovary color: Close to 144D.

*Seeds/fruits*.—Seed and fruit development have not been observed on plants of the new *Viburnum*.

Garden performance: Plants of the new *Viburnum* have been observed to have good garden performance and to tolerate rain and wind. Plants of the new *Viburnum* have been observed to be tolerant to USDA Hardiness Zone 7 and to high temperatures of about 35° C.

Pathogen/pest resistance: Plants of the new *Viburnum* have not been observed to be resistant to pathogens and pests common to *Viburnum*.

It is claimed:

1. A new and distinct *Viburnum* plant named 'Lisarose' as illustrated and described.

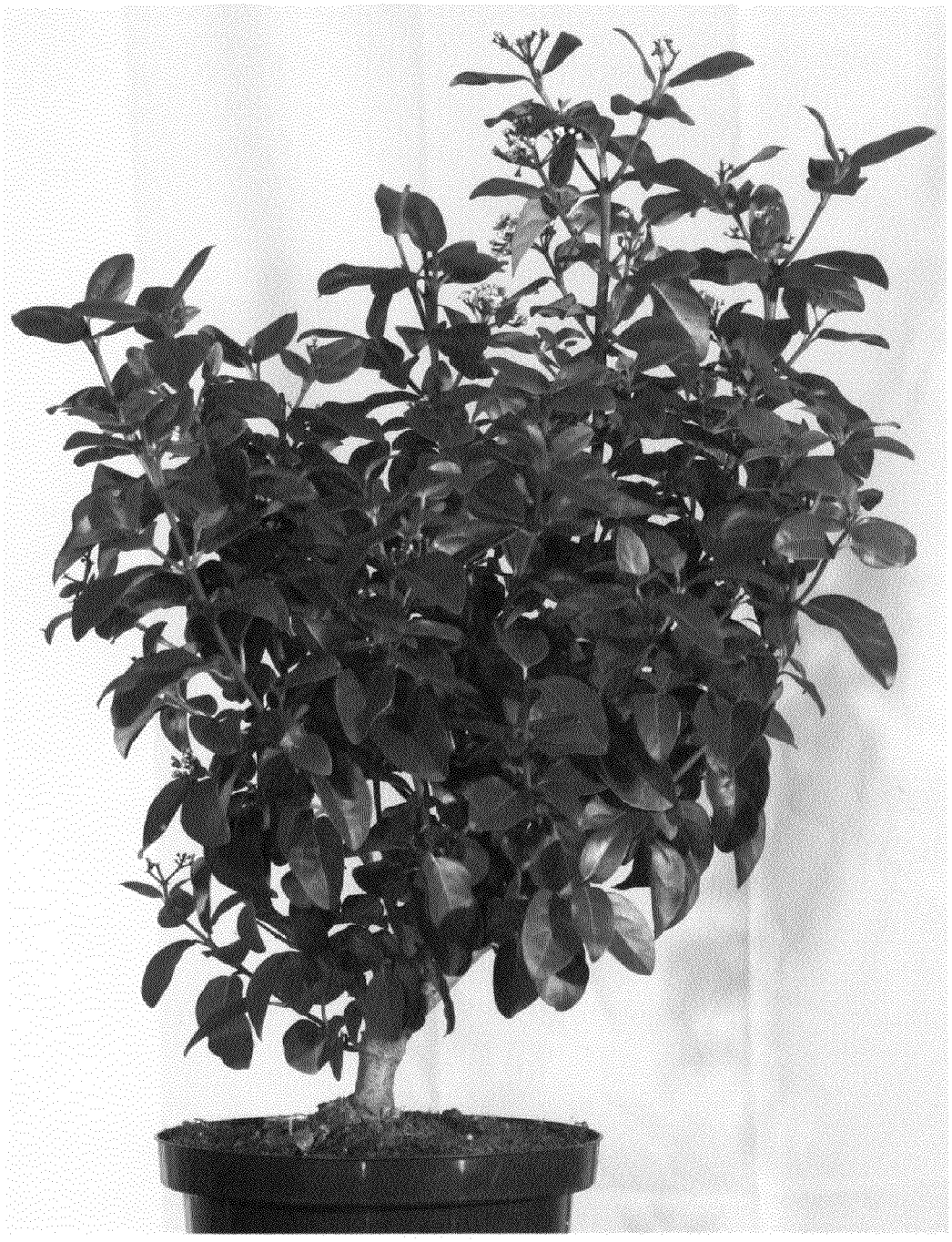

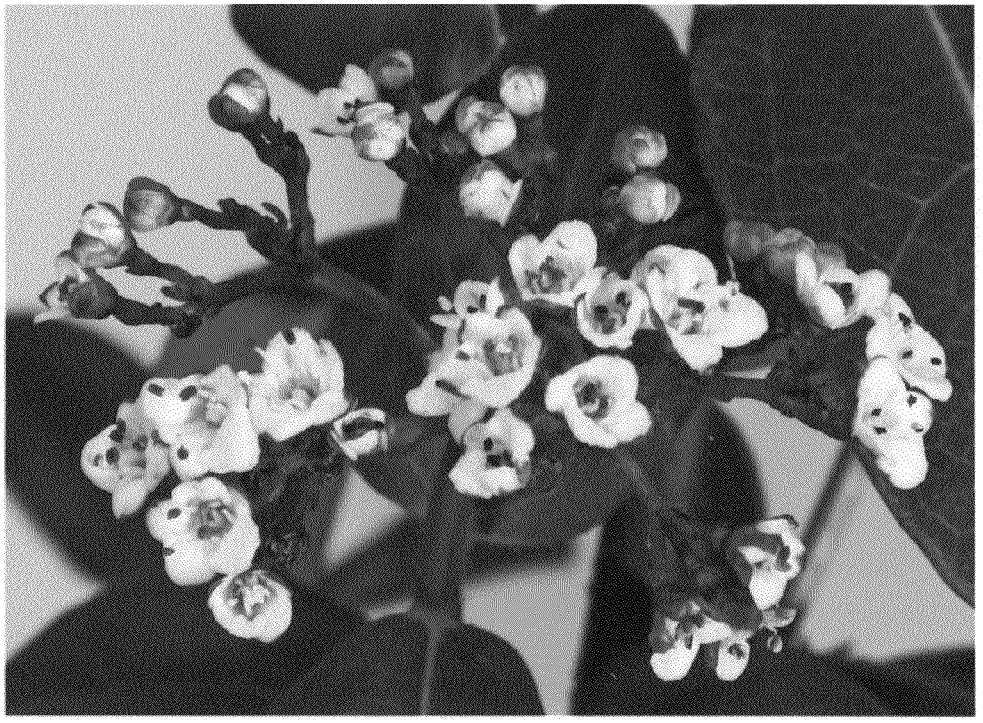

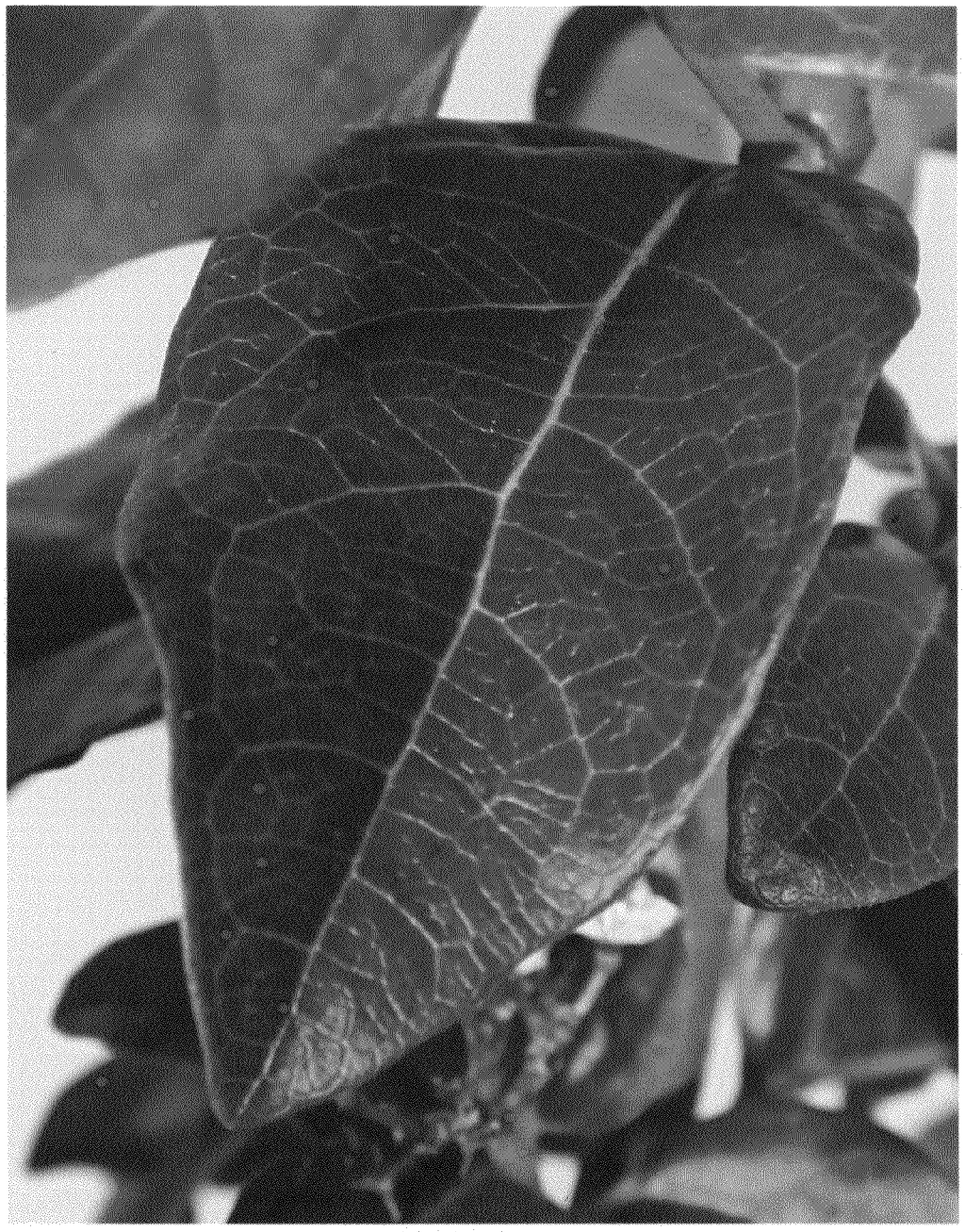

* * * * *